(12) United States Patent
Engel et al.

(10) Patent No.: US 8,684,967 B2
(45) Date of Patent: Apr. 1, 2014

(54) KINK RESISTANT CANNULA HAVING BUCKLE RESISTANT APERTURES

(75) Inventors: Rebecca Lynn Engel, Kalamazoo, MI (US); Donald R. Sandmore, Newaygo, MI (US); David Bruce DeWindt, Grand Rapids, MI (US); Frederick Alan Shorey, Jr., East Grand Rapids, MI (US); David Edward Weston, Rockford, MI (US)

(73) Assignee: Medtronic, Inc., Minneapolis, MN (US)

( * ) Notice: Subject to any disclaimer, the term of this patent is extended or adjusted under 35 U.S.C. 154(b) by 3798 days.

(21) Appl. No.: 10/890,960

(22) Filed: Jul. 14, 2004

(65) Prior Publication Data
US 2005/0033265 A1 Feb. 10, 2005

Related U.S. Application Data

(63) Continuation-in-part of application No. 10/619,932, filed on Jul. 15, 2003.

(60) Provisional application No. 60/487,393, filed on Jul. 15, 2003.

(51) Int. Cl.
*A61M 1/00* (2006.01)

(52) U.S. Cl.
USPC ........... 604/129; 604/6.05; 604/6.08; 604/39; 604/43; 604/44; 604/264; 604/523; 604/537; 604/540; 604/541; 604/542; 604/543; 604/544

(58) Field of Classification Search
USPC ............. 604/6.05, 6.08, 39, 43–44, 264, 523, 604/537, 540–544
See application file for complete search history.

(56) References Cited

U.S. PATENT DOCUMENTS

| 1,596,754 | A |   | 8/1926  | Moschelle |            |
|-----------|---|---|---------|-----------|------------|
| 2,268,321 | A | * | 12/1941 | Flynn     | 138/118    |
| 3,498,286 | A | * | 3/1970  | Koester et al. | 600/325 |
| 3,630,206 | A | * | 12/1971 | Gingold   | 604/103.08 |
| 3,833,003 | A | * | 9/1974  | Taricco   | 604/509    |

(Continued)

FOREIGN PATENT DOCUMENTS

| GB | 2 043 457 | 10/1980 |
|----|-----------|---------|
| WO | 01/21249  | 3/2001  |

OTHER PUBLICATIONS

*Stedman's Medical Dictionary*, 26th Edition, Williams & Wilkins, Baltimore MD, pp. 269 and 1674 (1995).

*Primary Examiner* — Nicholas Lucchesi
*Assistant Examiner* — Scott Medway

(57) ABSTRACT

A cannula has a body with a proximal end and a distal end and a tip on the distal end. The tip has an outer wall defining a lumen opening at the end of the tip and extending to the proximal end of the cannula. The tip further comprises one or more ribs extending into the lumen to support the outer wall from kinking when the cannula is flexed. The outer wall has a inner surface defining the lumen and a plurality of non-circular apertures formed in the tip extending into the lumen. The apertures having a major axis and a minor axis. The major axis aligned in relation to a circumference of the outer wall to prevent puckering or buckling when the tip is bent. This alignment is also designed to support the outer wall from kinking when the tip is bent.

9 Claims, 8 Drawing Sheets

(56) References Cited

U.S. PATENT DOCUMENTS

| | | | |
|---|---|---|---|
| 3,957,054 A | 5/1976 | McFarlane et al. | |
| 3,995,617 A | 12/1976 | Watkins et al. | |
| 4,038,489 A * | 7/1977 | Stenson et al. | 174/70 R |
| 4,596,564 A * | 6/1986 | Spetzler et al. | 604/541 |
| 4,639,252 A | 1/1987 | Kelly et al. | |
| 4,655,745 A * | 4/1987 | Corbett | 604/540 |
| 4,668,221 A * | 5/1987 | Luther | 604/164.03 |
| 4,680,029 A | 7/1987 | Ranford et al. | |
| 4,717,379 A | 1/1988 | Ekholmer et al. | |
| 4,808,158 A | 2/1989 | Kreuzer et al. | |
| 4,985,014 A | 1/1991 | Orejola | |
| 5,019,057 A * | 5/1991 | Truckai | 604/527 |
| 5,021,045 A | 6/1991 | Buckberg et al. | |
| 5,049,071 A * | 9/1991 | Davis et al. | 433/80 |
| 5,061,257 A | 10/1991 | Martinez et al. | |
| 5,180,364 A | 1/1993 | Ginsburg | |
| 5,180,387 A | 1/1993 | Ghajar et al. | |
| 5,188,619 A * | 2/1993 | Myers | 604/532 |
| 5,201,723 A | 4/1993 | Quinn | |
| 5,364,344 A | 11/1994 | Beattie et al. | |
| 5,403,291 A | 4/1995 | Abrahamson | |
| 5,478,309 A | 12/1995 | Sweezer et al. | |
| 5,507,751 A | 4/1996 | Goode et al. | |
| 5,531,717 A * | 7/1996 | Roberto et al. | 604/271 |
| 5,593,394 A | 1/1997 | Kanesaka et al. | |
| 5,599,291 A * | 2/1997 | Balbierz et al. | 604/8 |
| 5,766,135 A | 6/1998 | Terwilliger | |
| 5,782,811 A | 7/1998 | Samson et al. | |
| 5,792,116 A * | 8/1998 | Berg et al. | 604/202 |
| 5,797,869 A * | 8/1998 | Martin et al. | 604/43 |
| 5,817,071 A | 10/1998 | Dewindt et al. | |
| 5,817,074 A | 10/1998 | Racz | |
| 5,882,347 A * | 3/1999 | Mouris-Laan et al. | 604/524 |
| 5,947,953 A | 9/1999 | Ash et al. | |
| 5,976,114 A | 11/1999 | Jonkman et al. | |
| 5,984,908 A | 11/1999 | Davis et al. | |
| 6,024,730 A | 2/2000 | Pagan | |
| 6,036,654 A * | 3/2000 | Quinn et al. | 600/526 |
| 6,059,760 A * | 5/2000 | Sandmore et al. | 604/264 |
| 6,071,271 A | 6/2000 | Baker et al. | |
| 6,152,911 A | 11/2000 | Giannoble | |
| 6,246,914 B1 | 6/2001 | de la Rama et al. | |
| 6,264,645 B1 | 7/2001 | Jonkman | |
| 6,280,434 B1 | 8/2001 | Kinoshita et al. | |
| 6,435,189 B1 * | 8/2002 | Lewis et al. | 128/898 |
| 6,447,484 B1 | 9/2002 | Briscoe et al. | |
| 6,702,788 B2 * | 3/2004 | Kawakita et al. | 604/264 |
| 6,726,651 B1 | 4/2004 | Robinson et al. | |
| 6,827,710 B1 * | 12/2004 | Mooney et al. | 604/500 |
| 6,929,633 B2 * | 8/2005 | Evans et al. | 604/509 |
| 7,022,102 B2 * | 4/2006 | Paskar | 604/95.04 |
| 2002/0049402 A1 | 4/2002 | Peacock et al. | |
| 2002/0107506 A1 | 8/2002 | McGuckin et al. | |
| 2003/0144623 A1 | 7/2003 | Heath et al. | |
| 2004/0167478 A1 * | 8/2004 | Mooney et al. | 604/264 |
| 2005/0015072 A1 | 1/2005 | Engel et al. | |

* cited by examiner

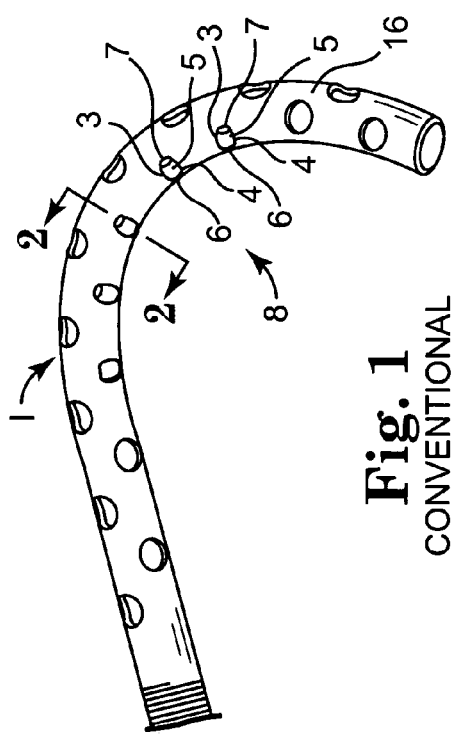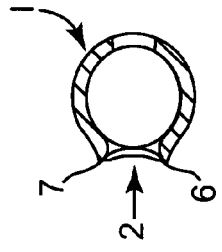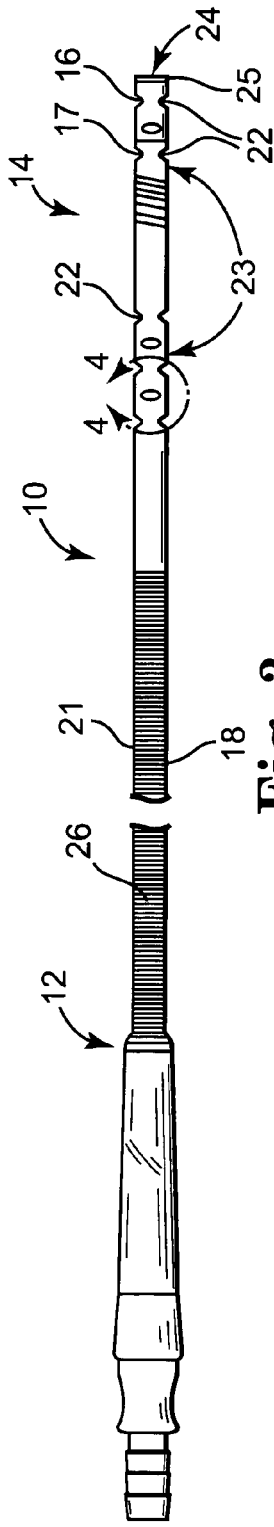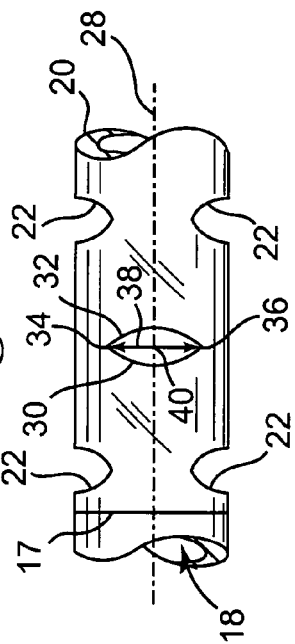

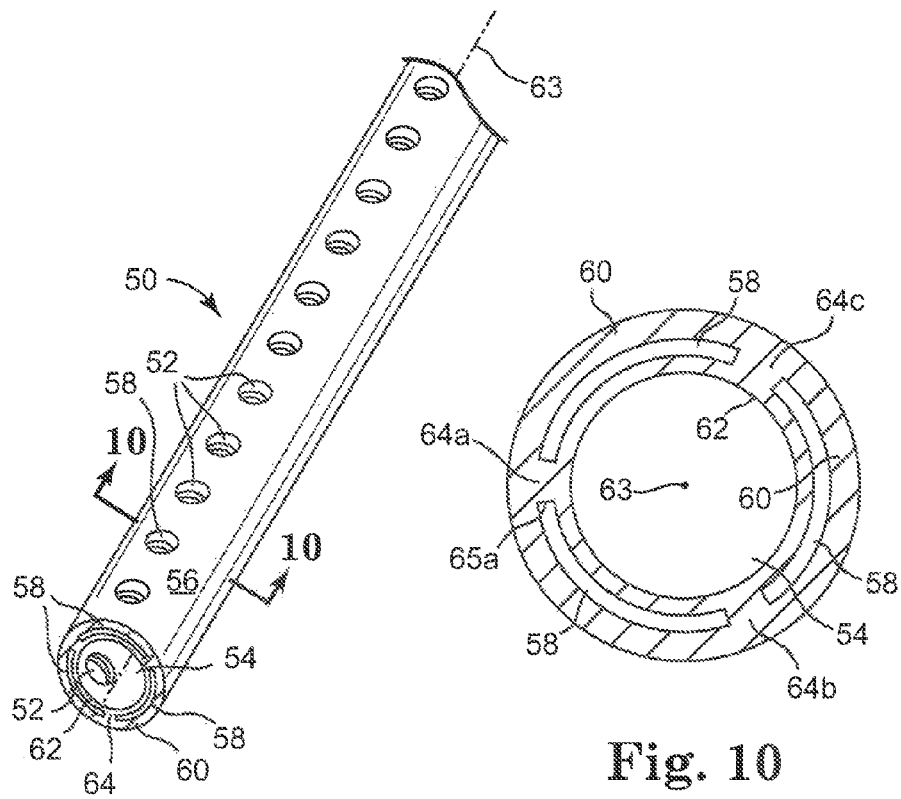
Fig. 9
Fig. 10
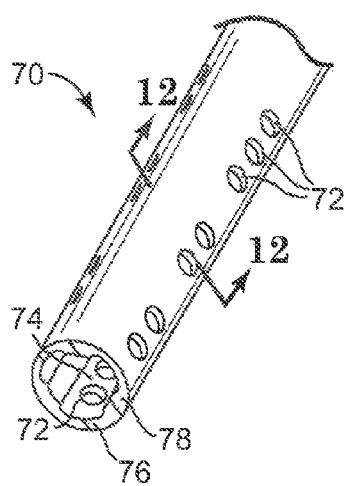
Fig. 11
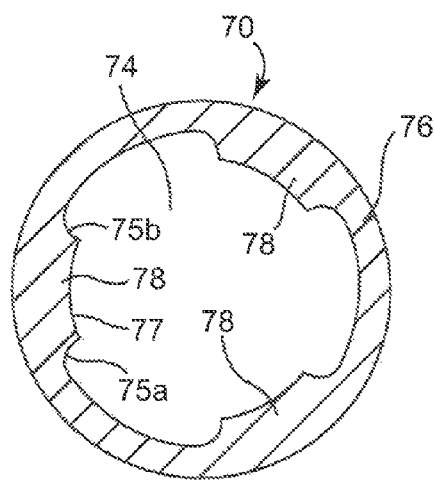
Fig. 12

KINK RESISTANT CANNULA HAVING BUCKLE RESISTANT APERTURES

CROSS-REFERENCE TO RELATED APPLICATIONS

This application claims the benefit of U.S. Provisional Patent Application No. 60/487,393, filed Jul. 15, 2003 and further, a continuation-in-part of U.S. non-provisional application Ser. No. 10/619,932, filed Jul. 15, 2003 both of which are incorporated herein by reference in their entirety.

FIELD OF THE INVENTION

The present invention relates to a medical cannula. In particular, the present invention relates to a cannula having apertures that are buckle resistant.

BACKGROUND OF THE INVENTION

During cardiac surgery, circulation of blood through a patient's body may be maintained by connecting the patient to an extracorporeal system, such as a heart-lung machine. The heart-lung machine adds oxygen to and removes carbon dioxide from the blood, heats or cools the blood, and provides impetus to the blood to cause the blood to circulate through the patient's vascular system.

Connecting a patient to an extracorporeal system is typically done by inserting a cannula into the patient's venous system near or in the heart to remove blood from the patient and direct it to the extracorporeal circuit. After the blood has passed through the extracorporeal circuit, the blood is infused into the patient's arterial system near the heart.

The venous cannula that is inserted into the heart to siphon blood away for entry into the heart-lung machine is typically inserted into the right atrium and/or vena cava. The venous cannula may be a single stage device having one set of input apertures or a multiple-stage device used to simultaneously drain the right atrium and superior vena cava through an atrial basket while the inferior vena cava is drained through another set of apertures at the distal tip of the cannula. Oxygenated blood is returned to the heart from the heart-lung machine using an arterial cannula positioned in the aorta.

Regardless of the type of surgical procedure in which a cannula is being used, the outside diameter of the cannula should be as small as possible with the largest possible inside diameter in order to maximize the flow of blood to and from the patient. The wall thickness of the cannula is therefore desired to be as thin as possible to maximize flow volume. However, a cannula must have the stiffness required to be inserted into the patient. The cannula may have to be flexed or bent as it is inserted into the proper location in a patient's body. The cannula must also be able to withstand negative pressure applied to the lumen without kinking/collapsing. The negative pressure occurs when blood is drawn from the patient from a gravity siphon, a vacuum assist, kinetic suction or the like, applied to the cannula to pull the blood into the extra-corporeal circuit.

Whether the cannula is being used to drain or insert fluids, it is desirable to maintain proper fluid flow through the cannula at all times. Accordingly, it is advantageous to minimize the wall thickness while preventing kinking of the tube. Kinking of a cannula occurs when a tube is flexed and results in the sides of the tube touching each other and folding in half, thus blocking or minimizing fluid flow through the interior lumen. Cannula materials, design, and aperture placement are chosen to minimize such kinking. Cannula may be made of different materials having a more resilient tip and a stiffer proximal section to accommodate handling. Additionally, external reinforcement has been used, such as a reinforcing spring integrated into the walls of the cannula, to prevent collapse of the lumen when the cannula is flexed.

Another challenge of cannula design is the minimization of buckling of the apertures in the walls of the cannula. Typically apertures are punched or drilled into the walls of a cannula to permit flow into or out of the lumen. Many apertures may be used in order to improve the drainage or perfusion characteristics of the cannula. When the cannula is flexed during placement of the cannula into the body, such as when inserting a cannula into the inferior vena cava or right atrium, the apertures may buckle. Buckling is the phenomenon of the sides of individual cannula apertures puckering outward when the cannula body is flexed. It is preferable to maintain a smooth outer surface on the cannula to minimize trauma to the tissue when the cannula is moved.

Referring to FIGS. 1 and 2, when a cannula 1 is flexed, aperture buckling can occur. The sides 3, 4 of individual apertures 5 on the concave side 8 are necessarily pushed toward one another as the cannula 1 is bent. As the sides 3, 4 close toward one another, the apertures 5 may buckle outward at other sides 6, 7.

The buckling phenomenon is undesirable because the portion of the aperture that buckles outward creates a scoop that extends outward from the cannula wall and may damage the sides of a vessel wall in the patient. For example, a venous cannula must be flexed as it is guided into the right atrium and the vena cava when performing a cardiopulmonary bypass procedure. It is desirable to minimize tissue damage to the internal vessel walls due to the puckering of apertures in the cannula as the cannula is placed into position. In addition, the doctor may adjust the cannula during a procedure to replace it into the desired location after manipulating the surrounding tissue to accommodate the procedure. For example, the doctor may lift and move the heart to allow visual access to the back of the organ for sewing. The cannula may slide out of position in this procedure and need to be adjusted. A buckled aperture interrupts the smooth outer surface of the cannula and may cause more trauma to the surrounding tissue if it is rubbed against a sidewall.

Conventional cannula designs attempt to minimize kinking of the cannula and buckling of flow apertures through the use of different materials such as the use of a hard plastic insert in the cannula that contains the flow apertures and a helical reinforcing spring to increase kink resistance. However, it is desirable to enhance cannula flexibility while also minimizing kinking of the cannula and buckling of the cannula apertures. A reinforcing wire is used to prevent kinking of the cannula in some designs but creates dimension limitations. It either reduces the flow for a given outside diameter cannula or increases the outside diameter required to achieve a desired flow. Therefore, it may be desirable to omit the reinforcing wire at the distal end of the cannula where the flow apertures reside. Simultaneously, it is desirable to maintain similar flow characteristics through the flow apertures while minimizing the chances of the apertures buckling when the cannula is bent or flexed.

There is a need for a cannula design that is flexible yet resistant to kinking. Further, there is a need for a cannula having flow apertures that resist buckling when the cannula is flexed. It would be desirable for a cannula design or method of cannula manufacture to provide one or more of these or other advantageous features. Other features and advantages will be made apparent from the present specification. The teachings disclosed extend to those embodiments that fall within the scope of the appended claims, regardless of whether they accomplish one or more of the aforementioned needs.

SUMMARY OF THE INVENTION

The invention relates to a cannula having a body with a proximal end and a distal end. A cannula tip is defined on the distal end. The body has a wall with a circumference defining a lumen extending from the proximal end to the tip. The lumen has a longitudinal axis and one or more apertures extending through the wall interconnected with the lumen. Apertures in the wall are formed to have a noncircular shape. The shape may be oval, elliptical, eye shaped or some other non-circular having a longer major axis and a shorter minor axis. The longer major axis may be perpendicular to the longitudinal axis of the lumen or similarly stated aligned along the circumference of the wall. The invention further relates to the strategic configuration of the apertures staggered in sets of a plurality of rows. Each row equally spaced radially from the others. Each set having one or more apertures in each row.

The invention further relates to a cannula having a body with a proximal end and a distal end and a tip on the distal end for engaging the heart as described above as a venous or arterial cannula. A lumen formed in the body extending from the proximal end to the tip forming a fluid path through the cannula. The cannula has one or more reinforcing ribs formed surrounding the lumen. The ribs prevent kinking to hold the lumen open. The ribs may be tapered or straight and extend from the body inward towards a longitudinal axis of the lumen. The ribs may have a top having a concave, rounded or flat shape. The ribs may be interconnected by a link forming an inner wall around the lumen and a fluid passageway between the ribs. The link may have a concave surface forming a smooth bore around the lumen. The fluid passageways may be pressurized from an outside source to provide support to the sidewall of the tip. The cannula further may be configured as a venous cannula having a plurality of non-circular apertures in the wall.

Further still, the invention relates to a method of making a cannula. The method includes the steps of forming a cannula body having a wall defining a lumen and bending the cannula body at the tip in a first direction such that the cannula body has a concave side and a convex side. The method further includes the steps of punching an aperture into the concave side of the body using a non-circular punch and then straightening the cannula body. The apertures may be molded or formed otherwise resulting in an aperture having a side wall that will not buckle outward when the cannula is flexed at or near the aperture.

The ribs are molded with the tip. The ribs are of the same [or different] resilient material as the tip. The tip may also be reinforced with a wire wound helically on or in the wall of a portion of the tip. The wire may be molded into the tip wall. The wire or a barium strip or similarly radio opaque material may be added to the tip for locating the tip with x-ray or other non-invasive sensing technology.

The invention is capable of other embodiments and of being practiced or being carried out in various ways. Alternative exemplary embodiments relate to other features and combinations of features as may be generally recited in the claims.

BRIEF DESCRIPTION OF THE DRAWINGS

The invention will become more fully understood from the following description, taken in conjunction with the accompanying drawings, wherein like reference numerals refer to like elements, in which:

FIG. 1 is a perspective view of a conventional cannula in a flexed configuration.

FIG. 2 is a sectional view taken generally along line 2-2 of FIG. 1.

FIG. 3 is an elevation view of a cannula according to a first embodiment of the invention.

FIG. 4 is an enlarged detail elevation view of a segment of the distal end of the cannula shown in FIG. 3, the segment location generally indicated by line 4-4 of FIG. 3.

FIG. 9 is a perspective view of a segment of a cannula body according to an alternative embodiment having additional fluid passages.

FIG. 10 is a sectional view taken generally along line 10-10 of FIG. 9 illustrating additional fluid passages.

FIG. 11 is a perspective view of a segment of a cannula body according to an alternative embodiment.

FIG. 12 is a sectional view taken generally along line 12-12 of FIG. 11 illustrating the supporting ribs.

DETAILED DESCRIPTION OF PREFERRED EMBODIMENTS

Figure 5:
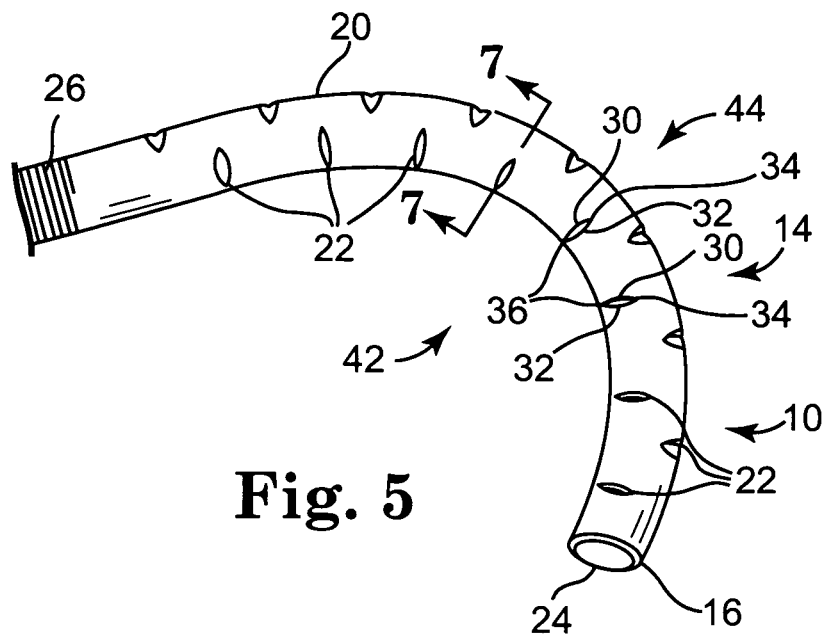
FIG. 5 is a perspective view of the distal end of the cannula of FIG. 3, shown in a flexed configuration.

A conventional catheter or cannula 1 having a flexible tip 16 is shown in FIG. 1. The tip 16 has a plurality of holes 5 that are shown buckling causing an edge to push outward like a scoop, from the profile of the tip at portions 6 and 7. The sides 3, 4 of individual apertures 5 on the concave side 8 are necessarily pushed toward one another as the cannula 1 is bent. As the sides 3, 4 close toward one another, the apertures 5 may buckle outward at other sides 6, 7 as shown in FIG. 2.

Referring to FIG. 3, a catheter or cannula, shown as, but not limited to, venous cannula 10 has a body 21 with a proximal end 12, a distal end 14 and a tip 16. The tip 16 is located at the distal end 14 of the cannula 10 and a lumen 18 formed in the body 21 extends through the cannula 10 from the proximal end 12 to the tip 16. The wall 20 has a circumference 17.

The lumen 18 may be open at the proximal end 12 to be connected to a cardiac bypass system such as a heart-lung machine. In a venous cannula 10, the distal end 14 includes a number of holes or apertures 22 in the wall 20 to pass blood from the heart to the lumen 18 and through the cannula body 21 into a heart-lung machine. In both an arterial cannula 10 and a venous cannula 10 a distal aperture 24 may be provided in the end 25 of the tip 16 of cannula 10. Various methods of performing a cardiopulmonary bypass are known in the art. In the embodiment depicted in FIG. 3, the cannula 10 is a dual stage venous cannula 10. In other embodiments, the cannula 10 may be of other types, such as a venous cannula 10 having a staggered set of apertures 22 used to drain two portions of the heart simultaneously. Each set may have two or more apertures to resist kinking of the wall 20.

Further referring to FIG. 3, a reinforcement member, shown as helical reinforcement spring 26 may extend over a substantial portion of a length of body 21 to prevent kinking or closing off of the lumen 18 when the device is flexed, bent, or otherwise manipulated when in use by a surgeon. In the two-stage cannula 10 a distal set of apertures 22 is positioned at the end 25 of the tip 16 and a proximal set of apertures 22 is positioned between the end 25 and the body 21. A reinforcement member 26 may be disposed on the tip between the distal apertures and the proximal apertures 22. The end 25 has a tapered or rounded shape to facilitate insertion into the patient.

Referring to FIG. 4, the one or more apertures 22 in fluid communication with the lumen 18 are non-circular. The apertures 22 may be oval, elliptical, egg or eye-shaped. As defined herein, eye-shaped means aperture 22 is defined by first arcuate portion 30 and second arcuate portion 32 that intersect with one another at two tips or corners 34, 36. Aperture 22 is formed to resist buckling by aligning a longer major axis 38 and a shorter minor axis 40 in a predetermined relation to the circumference 17 of the body 21 or longitudinal axis 28 of the lumen 18.

In a preferred embodiment, apertures 22 are disposed such that the major axis 38 is aligned with the circumference 17. The minor axis 40 is parallel to the longitudinal axis 28 of lumen 18. The placement of apertures 22 to orient the major axis 38 at a right angle to longitudinal axis 28 is intended to increase the resistance to buckling of apertures 22 and to increase the resistance to kinking of wall 20 when the cannula 10 is flexed. In the embodiment depicted in FIGS. 3 and 4, apertures 22 are oriented such that major axis 38 is perpendicular to the longitudinal axis 28. However, in other embodiments, a selected number of apertures 22 may be oriented in different relationships between the lumen axis 28 aperture major axis 38 and minor axis 40. For example, apertures 22 may be oriented such that major axis 38 is perpendicular to longitudinal axis 28 at locations where the cannula 10 exhibits the greatest degree of bending during use in surgery, and therefore presents the greatest need for buckle-resistant apertures 20.

For example, placing a set of apertures 22 near the tip 16 and separated from a more proximal group of apertures 22 by a continuous wall 18 segment without apertures 22 creates a dual stage cannula 10 used to drain two portions of a patient's heart simultaneously. The continuous wall 18 segment may extend a distance of approximately 1 to 2 inches along the cannula body 21 between the sets of apertures. A reinforcing member 26 may be on or molded into the continuous wall 18 segment between the sets of apertures 22. Further still, the size and placement of apertures 22 differs depending on the use of the cannula 10, for example whether the cannula 10 is a venous drainage cannula or an arterial perfusion cannula 10.

Cannula 10 may be made of various materials that are biocompatible and manufactured by various methods such as extrusion, injection molding, or assembly of component parts. Exemplary materials include polyvinyl chloride (PVC), plastisol, and polyurethane. In a preferred embodiment, cannula 10 is made of polyurethane using an extrusion process. In the process, a first layer of the cannula wall 20 is extruded. The reinforcement spring 26 is slipped over the first wall 20 portion and followed by the extrusion of additional material over the top of the reinforcement spring 26 to enclose the reinforcement spring 26 in the cannula wall 20. After the major steps are performed to create the wall 20 and reinforcement spring 26 structure, apertures 22 may be added. Another method of making a cannula is a dip-molding process using a mandrel dipped in a material such as plastisol or polyurethane.

Cannula 10 may be made with the tip 16 made from a different, more flexible material than the body 21. The parts can be joined in the molding process, by welding or other fastening method known for connecting dissimilar materials.

Figure 6:
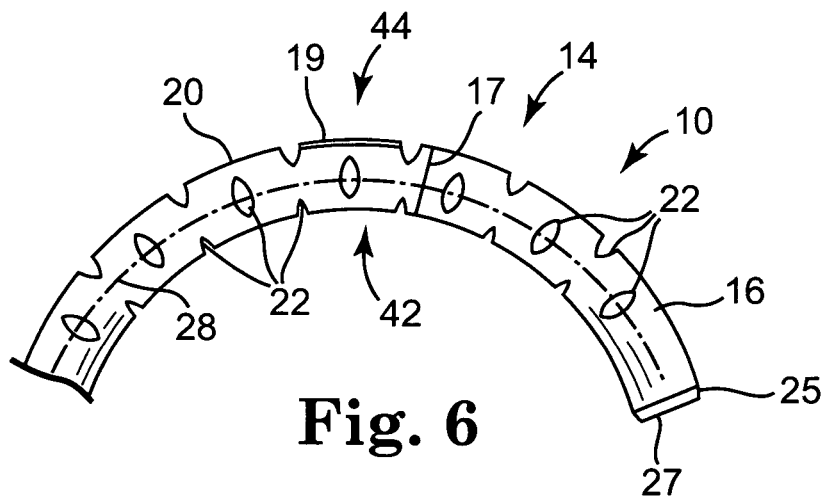
FIG. 6 is an elevation view of the cannula of FIG. 3, shown in a flexed configuration.
Figure 7:
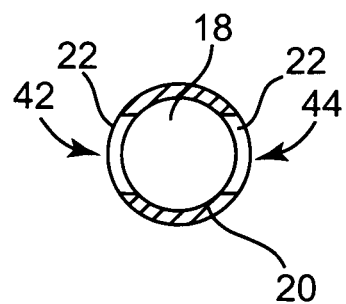
FIG. 7 is a sectional view taken generally along line 7-7 of FIG. 5.

Referring to FIGS. 5 and 6, when cannula 10 is flexed, apertures 22 on the concave side 42 of flexed cannula 10 close to a certain degree in order to accommodate the bunched wall 20 material on the concave side 42. Apertures 22 on convex side 44 stretch open when cannula 10 is bent or flexed. Permitting apertures 22 to accommodate the bunched wall material on concave side 42 by closing aids in preventing kinking of cannula 10 by taking up the stress in the tube wall 20 on the concave side of the body 21. The apertures 22 are positioned in a pattern of staggered, two aperture sets 23 (FIG. 3).

In the exemplary embodiment depicted in FIGS. 3-7, eye-shaped apertures 22 exhibit buckle resistant properties. The reduction in buckling is accomplished because first and second arcuate portions 30, 32 of each aperture 22 are able to close toward one another while the stress is taken up at corners 34, 36. Corners 34, 36 do not buckle, in contrast to the conventional design depicted in FIG. 1 where the aperture sides 6, 7 on the concave side 8 buckle when the cannula 10 is flexed. The cannula 10 retains a smooth exterior on the body 21 to facilitate insertion, adjustment and removal in the flexed or unflexed shapes. Kinking is prevented because the arcuate portions 30, 32 act as supports to hold the portions of the wall 20 adjacent the corners 34, 36 spaced from each other thus keeping the lumen 18 open.

Figure 8:
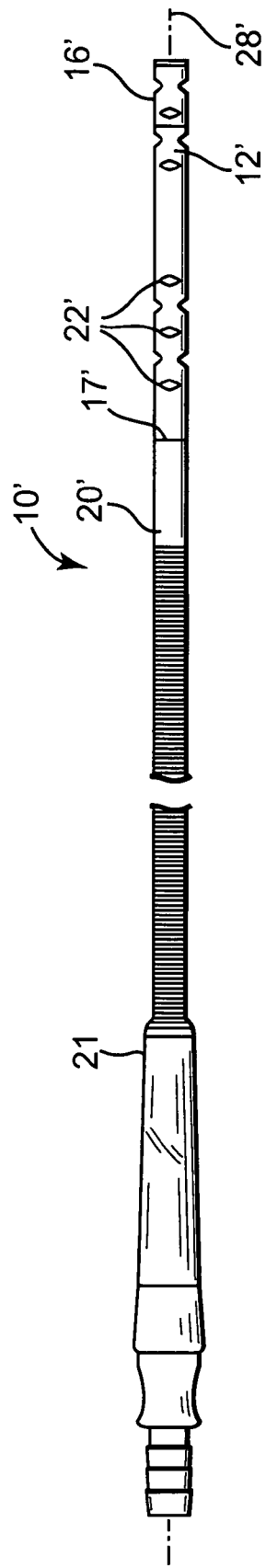
FIG. 8 is an elevation view of a cannula according to a second embodiment of the invention.

In the exemplary embodiment of FIG. 8 with diamond shaped apertures 22' placed in the wall 20. The apertures 22' are oriented along the body 21 having their long dimension transverse to the longitudinal axis 28' to preserve the structural integrity of cannula 10' when cannula 10' is flexed. In the depicted embodiment, cannula 10' has four rows of apertures 22' extending along the longitudinal axis 28' of the lumen 18. The rows are evenly spaced such that each row is 90 degrees apart from adjacent rows and non-adjacent rows are 180 degrees apart from one another. Adjacent rows are staggered such that apertures 22' are not placed immediately next to one another, each aperture 22' in adjacent rows being a different distance from tip 16'. The staggered aperture placement increases the area of wall 20' between adjacent apertures 22', thus increasing structural integrity of the cannula body 21' and therefore increasing resistance to kinking. In the exemplary embodiment, rows radially separated around the circumference 17' with the apertures 22' aligned parallel to the longitudinal axis 28'.

In other embodiments, the apertures 22 may be placed on the cannula body 21 in different patterns, such as in a spiral configuration around the axis 28 or including more or fewer rows extending along the body 21. Further, the size of the individual apertures 22 may differ from that depicted in the figures. The doctor may place the cannula having the apertures 22 positioned to facilitate different functions of the cannula 10.

Referring to FIGS. 9 and 10, a reinforced wall 56 is shown in an alternative exemplary embodiment configured to resist kinking. The wall 56 in segment 50 of cannula 10 includes outer wall 60, inner wall 62, ribs 64, interior channel 58 and apertures 52. The ribs 64 are supports or ridges formed in the wall 56 to resist kinking. The apertures 52 are formed in the outer wall 60 to the lumen 54 connecting with the interior channel 58. Apertures 52 are shown extending through both the outer wall 60 and the inner wall 62 but alternatively may extend through the rib 64 thus keeping the interior channel 58 isolated from the lumen 54. The apertures 52 are configured in any number of different shapes and sizes. The wall 56 includes interior channels 58 between an outer wall 60 and inner wall 62. The interior channels 58 are fluid passageways along the tip 16 intended to provide an alternate flow path to the lumen 54 and may extend from the tip end 25 to the proximal end 12 of the body 21 in parallel to the lumen 54 to maintain flow through the cannula 10 in the case of an obstruction in the lumen 54 or a kink in the cannula 10. The cannula 50 remains flexible when the outer wall 60 thickness is reduced because of the addition of the supporting ribs 64 to prevent kinking. Ribs 64 extend outward from the outer wall and are inter connected by links or wall segments 68 forming the inner wall 62 defining lumen 54 having longitudinal axis 63. Interior channel 58 is formed between adjacent ribs 64 and the outer and inner walls 60, 62.

Figure 10A:
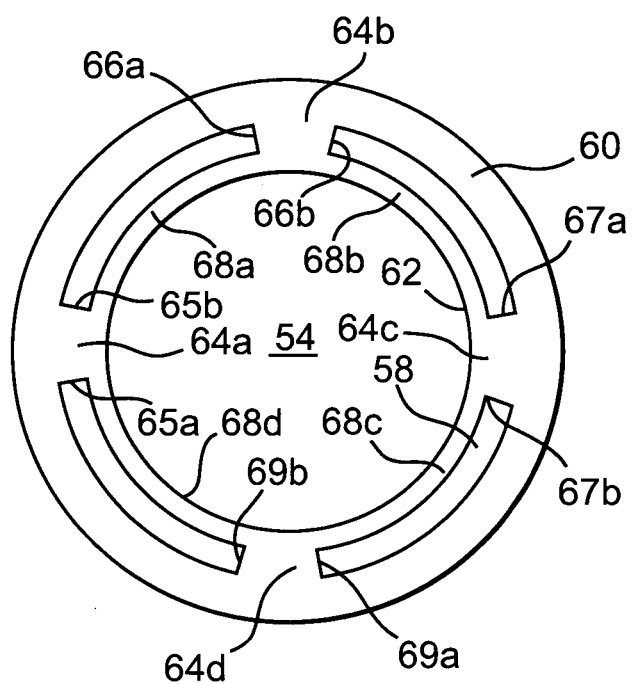
FIG. 10a is a sectional view of an alternate embodiment.

A section of an alternate embodiment is shown in FIG. 10a with outer wall 60 having first rib 64a, second rib 64b, third rib 64c and fourth rib 64d. The four ribs 64a, 64b, 64c and 64d are equally spaced radially around the axis 63 of the lumen 54. First rib 64a comprises a first side 65a and second side 65b. Second rib 64b comprises first side 66a and second side 66b. Third rib 64c comprises first side 67a and second side 67b. The fourth rib 64d comprises a first side 69a and a second side 69b. First wall segment 68a extends from the second side 65b of first rib 64a to the first side 66a of second rib 64b. Second wall segment 68b extends from the second side 66b of second rib 64b to the first side 67a of third rib 64c. Third wall segment 68c extends from the second side 67b of third rib 64c to the first side 69a of fourth rib 64d. Fourth wall segment 68d similarly extends between the fourth rib 64d and first rib 64a to arcuately join with the other wall segments 68a, 68b, 68c to form a smooth inner wall 62 defining the lumen 54.

Referring to FIG. 10a the ribs are disposed at approximately 90 degrees relationship with adjacent ribs. It should be understood, the ribs used to support the lumen 54 may number two or more when configured with an interconnecting wall segment 68a-d defining inner wall 62.

Referring to FIGS. 11 and 12, in an alternative exemplary embodiment, a segment of a tip 16 is shown comprising apertures 72, a lumen 74, support 78 and a wall 76. The supports 78 extend from the wall 76 into the lumen 74 between rows of apertures 72. FIGS. 11 and 12 illustrate three rows of apertures 72 however, one or more rows may be used. The apertures 72 may be formed through the supports 78 or between adjacent supports 78. The cannula 70 has enhanced flexibility because the thickness of the wall 76 is reduced between supports 78. The supports 78 provide buttress to the wall 76 to reduce kinking. Each support has a first side 75a and a second side 75b and a top 77. The top 77 has a concave shape with respect to the lumen to provide a smooth inner wall defining the lumen 74. The first side 75a and second side 75b each has an arcuate cross sectional shape to having a sloped relation with the body to ease molding and provide a smooth inner wall defining the lumen 74. The apertures 72 are shown in a spaced set configuration.

Figure 12A:
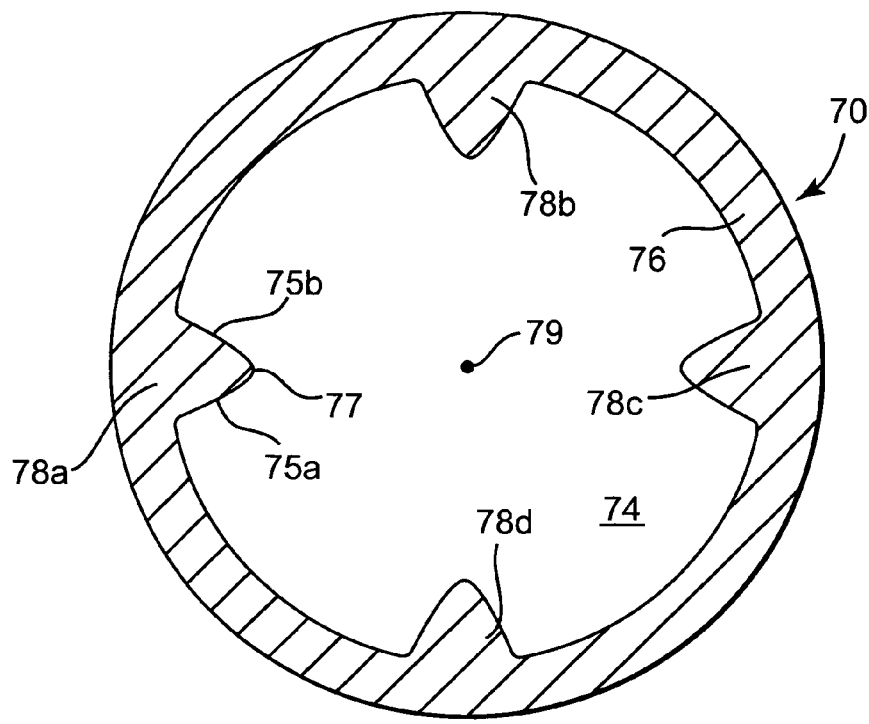
FIG. 12a-b is a sectional view of an alternate embodiment of the supporting ribs.

Referring to FIG. 12a, four supports 78a-d are shown each having a top 77 with a rounded point shape. The rounded shape top 77 extending between the first side 75a and the second side 75b. The first side 75a having an arcuate shape with a convex portion extending into the lumen 74 forming a sloped relation with the body 21.

Figure 12B:
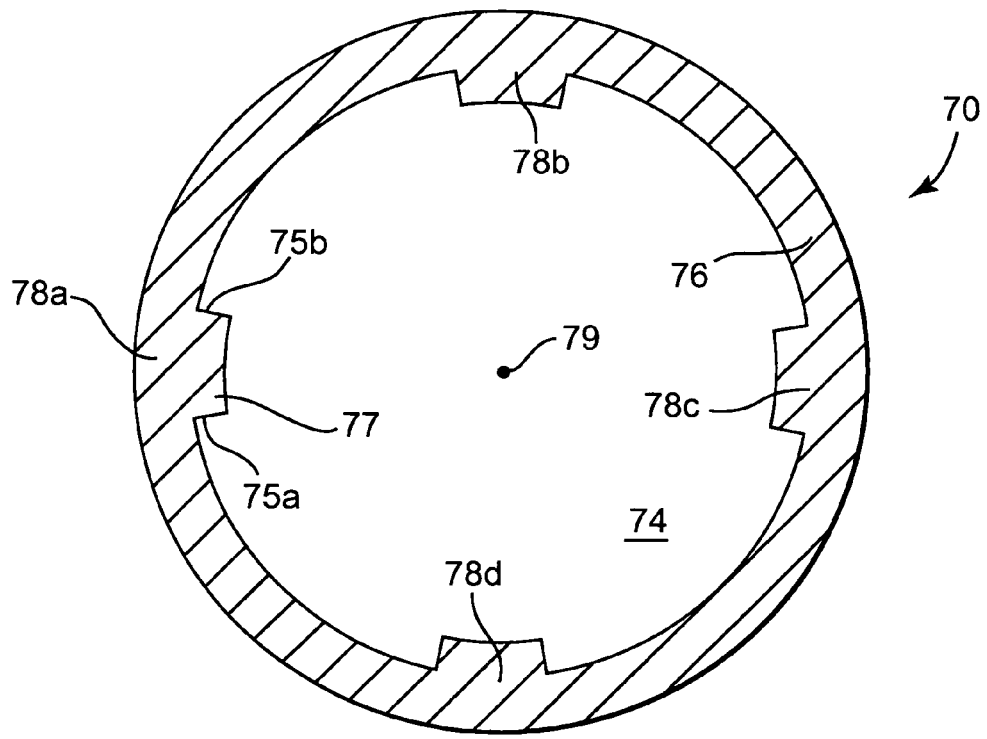
Figure 13:
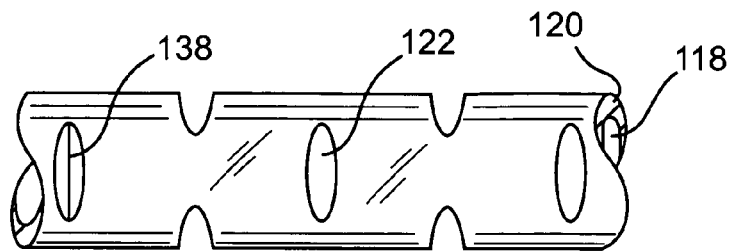
FIG. 13 is an elevation view of a cannula according to another embodiment of the invention.

Referring to FIG. 12b, a plurality of supports 78a-d are illustrated having a straight first side 75a and a straight second side 75b defining the lumen 74. The top 77 of each support is arcuate in a concave configuration with respect to the lumen axis 79. The top 77 defining the inside of the lumen 74 may also be flat or parallel to a tangent to the lumen axis 79.

Cannula 10, 50 and 70 may be made by an extrusion process. A cannula 50, 70 made via extrusion presents design challenges because the extruded product has a constant cross-section. The tip design shown in FIGS. 1-19 is advantageous because the cannula wall does not vary in cross-section over the length of the segment. The apertures are added after the wall has been extruded. In other embodiments, cannula 10, 50, 70 may be made by injection molding or dip-molding.

After the cannula body 21 is formed, apertures 22 are added into wall 20 to allow communication between the lumen 18 and the exterior of cannula 10 using a punch or drill process. Eye-shaped holes do not lend themselves to a drilling process. Eye-shaped punch may be used to add apertures 22 through cannula wall 20. In certain cases, the distal end of the cannula 10 may be a separate piece such as a tip 16 portion with apertures, with or without a reinforcing spring. The tip 16 is attached to the proximal end of the cannula 10 at a later stage of the manufacturing process by a known process such as by RF welding.

In an exemplary embodiment, a method of punching apertures 22 minimizes the possibility of apertures 22 buckling when cannula 10 is flexed. In this embodiment, apertures 22 are punched into the concave side 42 of cannula 10 while cannula 10 is bent or flexed. An oval punch may be most suitable for this method, however, the method also applies to a round punch used to make substantially circular apertures.

Figure 14:
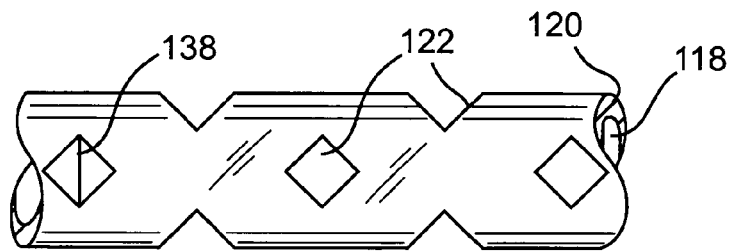
FIG. 14 is an elevation view of a cannula according to another embodiment of the invention.
Figure 15:
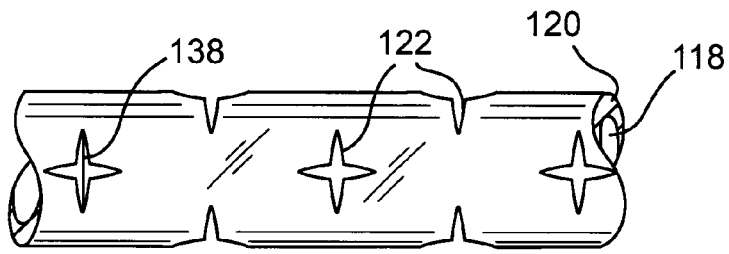
FIG. 15 is an elevation view of a cannula according to another embodiment of the invention.
Figure 16:
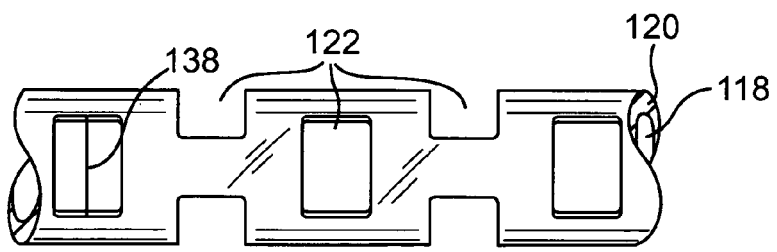
FIG. 16 is an elevation view of a cannula according to another embodiment of the invention.
Figure 17:
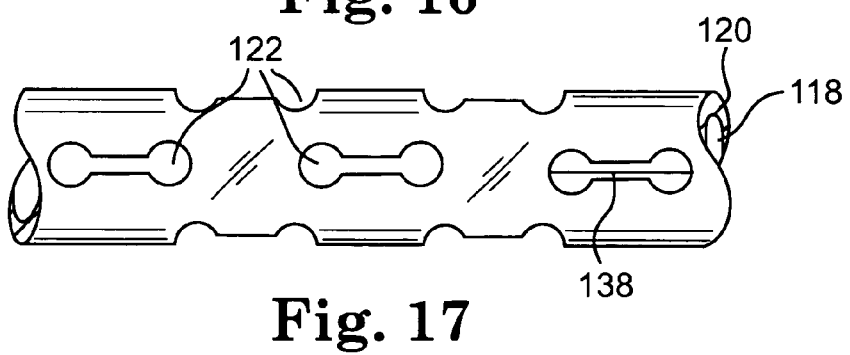
FIG. 17 is an elevation view of a cannula according to another embodiment of the invention.

Referring to FIG. 14, in an exemplary embodiment, cannula 100 includes diamond-shaped apertures 122 that are oriented such that a longer major axis 138 of each aperture 122 is oriented at a right angle to the longitudinal axis 128 of lumen 118. Apertures 122 are intended to exhibit buckle resistant properties and may be placed on the cannula wall 20 in similar patterns to those described herein with respect to the other described cannula embodiments.

Referring to FIGS. 13-17, in other alternative exemplary embodiments, the apertures 122 may be other shapes that also exhibit buckle resistant properties. While the apertures are generally shown having the longer axis portion 138 of the apertures 122 oriented perpendicular to the cannula lumen 118, such an orientation may not be required. Instead, selected aperture 122 shapes may be buckle resistant due to the shape of the aperture 118 regardless of orientation on the cannula wall 120. The manufacturing method of punching while holding the cannula 10 in an arcuate shape predisposes the longitudinally oriented sides 103, 104 of the aperture 122 at an acute angle 123 to a diameter of the cannula 110.

Figure 18:
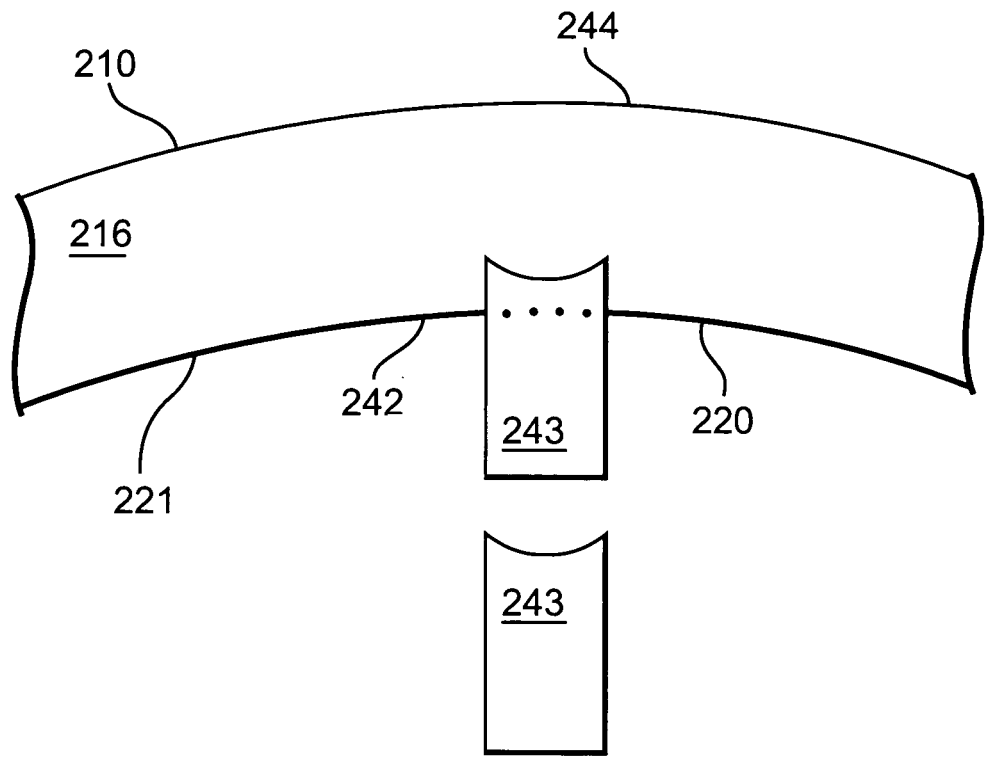
FIG. 18 is a section view of FIG. 6 taken along the axis, illustrating a flexed cannula in an arcuate shape for engagement with the punch.
Figure 19:
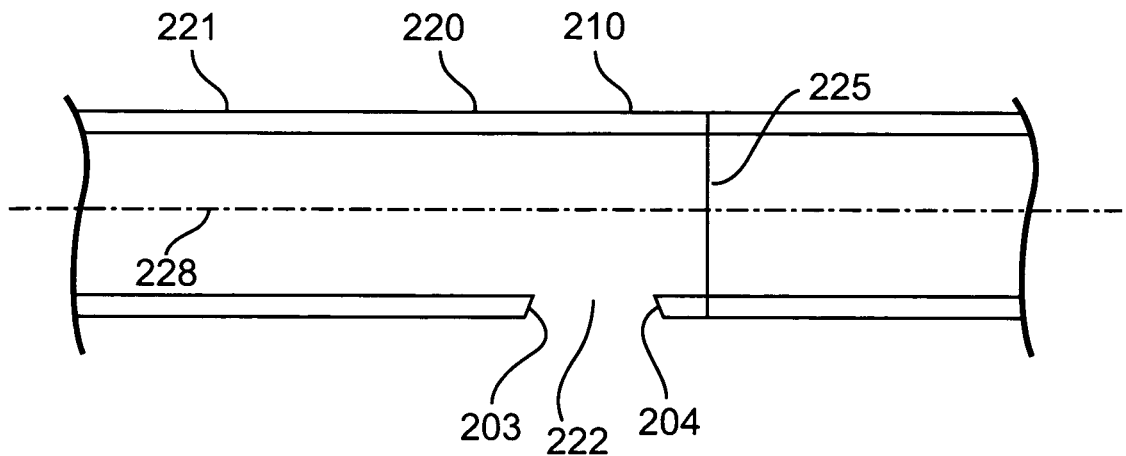
FIG. 19 is a section view of the cannula of FIG. 18 after the punch has formed an aperture, the cannula straightened to show the cut angle of the apertures.

Referring to FIGS. 18 and 19, the apertures 222 may be punched individually such that each aperture 222 is punched while the cannula 210 has been flexed into a flexed position. As disclosed, the apertures 222 are formed by a punch 243 (shown in outline in FIG. 18) pushed through the wall 220 after bending the cannula 210 into an arcuate shape along a form (not shown). The punch 243 is applied at the apex of the concave side 242. An anvil (not shown) is inserted into the tip 216 to prevent the wall 220 adjacent the convex side 244 from being punched as well. The cannula 210 is then straightened out (FIG. 19) and apertures 222 is stretched somewhat as the concave side 42 wall 221 material regains its original length. The sidewalls 203 and 204 of the aperture 222 are formed at an acute angle to a diameter 225 of the cannula 222. When cannula 210 is later flexed, such as during a surgical procedure, apertures 22 on the concave portion 42 of the curve assume the shape of the original punched holes rather than buckling as may occur in other designs.

When the above-described manufacturing method is utilized to create apertures, a punch used to create a circular, oval or elliptical aperture may be suitable to minimize buckling without requiring an eye-shaped punch. Note that it may be preferable to punch one row of apertures at a time into the cannula wall along the concave portion of the flexed cannula to achieve best results.

The orientation of non-circular apertures such that the longer major axis of each aperture extends at a right angle to the lumen longitudinal axis may be advantageous as a feature used to minimize buckling or kinking with several shapes of apertures used on a single tip 216. Eye-shaped apertures are shown in FIGS. 3-6; however, other non-circular apertures 22, 122, 222 also derive the benefit of the depicted orientation. For example, an oval aperture may exhibit reduced buckling tendencies when aligned such that the longer major axis is parallel to the circumference of the cannula when formed using this method. Further, an oval aperture may be sized to provide a similar flow rate to a similarly sized circular aperture while also deriving the benefit of reduced buckling due to the described orientation.

For example, while a venous cannula is shown incorporating the various aspects of the invention, the invention may also be applicable to arterial cannulae, cardioplegia cannulae, or other cannula or catheter designs that derive a benefit from reduced kinking and aperture buckling properties. Other examples may include femoral access cannulae and tubes used in neurological applications such as brain perfusion tubes. Such cannulae are available in many sizes and shapes and are used in different types of surgical procedures. Furthermore, other substitutions, modifications, changes, and omissions may be made in the design, operating conditions, and arrangements of the exemplary embodiments without departing from the scope of the invention as expressed in the appended claims.

While the detailed drawings and specific examples given herein describe various exemplary embodiments, they serve the purpose of illustration only. It is to be understood that the invention is not limited in its application to the details of construction and arrangements of components set forth in the preceding description or illustrated in the drawings.

What is claimed is:

1. A cannula, comprising:
a body comprising a lumen, a proximal end, and a distal end comprising a flexible tip comprising an outer wall and an inner wall, wherein the outer wall comprises a plurality of non-circular apertures in fluid communication with the lumen;
wherein the lumen comprises a longitudinal axis; and
the outer wall comprises a plurality of ribs that hold the inner wall in spaced relation to the outer wall to prevent kinking and provide support to prevent the tip from kinking when the tip is flexed;
wherein the outer wall, the inner wall and the ribs combine to define a first channel between the outer and inner walls, and further wherein a first one of the apertures extends through the outer wall, the first channel and the inner wall such that the first aperture is fluidly open to the first channel and the lumen.

2. The cannula of claim 1, wherein the channel functions as a fluid passageway.

3. The cannula of claim 1, wherein each rib comprises a first side extending into the lumen and a second side extending into the lumen.

4. The cannula of claim 1, wherein the ribs are evenly distributed radially around the axis of the tip.

5. The cannula of claim 1, wherein apart from the plurality of apertures, the inner wall has a continuous circumference in defining the lumen along the tip.

6. The cannula of claim 1, wherein the plurality of ribs includes first, second and third ribs, the first and second ribs defining opposing sides, respectively, of the first channel, and further wherein the body defines a second channel between the inner wall and the outer wall, the second and third ribs defining opposing sides, respectively, of the second channel.

7. The cannula of claim 6, wherein a second one of the apertures extends through the outer wall, the second channel, and the inner wall such that the second aperture is fluidly open to the second channel and the lumen.

8. The cannula of claim 7, wherein the body further defines a third channel between the inner and outer walls, the third channel being separated from the first and second channels by at least one of the first-third ribs, and further wherein a third one of the apertures extends through the outer wall, the third channel, and the inner wall such that the third aperture is fluidly open to the third channel and the lumen.

9. The cannula of claim 1, wherein the body defines a plurality of channels between the inner and outer walls, the plurality of channels including the first channel, and further wherein each of the apertures extends through the outer wall, the inner wall and one of the plurality of channels such that each of the apertures is fluidly open to the lumen and one of the plurality of channels.

* * * * *